(12) United States Patent
Nino

(10) Patent No.: US 11,306,801 B2
(45) Date of Patent: Apr. 19, 2022

(54) SINGLE USE GEAR REDUCTION DEVICE

(71) Applicant: ECA Medical Instruments, Inc., Newbury Park, CA (US)

(72) Inventor: John Nino, Newbury Park, CA (US)

(73) Assignee: ECA MEDICAL INSTRUMENTS, INC., Thousand Oaks, CA (US)

( * ) Notice: Subject to any disclaimer, the term of this patent is extended or adjusted under 35 U.S.C. 154(b) by 10 days.

(21) Appl. No.: 17/053,998

(22) PCT Filed: Nov. 2, 2018

(86) PCT No.: PCT/US2018/059048
§ 371 (c)(1),
(2) Date: Nov. 9, 2020

(87) PCT Pub. No.: WO2019/090142
PCT Pub. Date: May 9, 2019

(65) Prior Publication Data
US 2021/0215231 A1      Jul. 15, 2021

Related U.S. Application Data

(60) Provisional application No. 62/580,936, filed on Nov. 2, 2017.

(51) Int. Cl.
*F16H 1/32* (2006.01)
*B25B 17/00* (2006.01)
(Continued)

(52) U.S. Cl.
CPC ............... *F16H 1/32* (2013.01); *B25B 17/02* (2013.01); *F16H 57/082* (2013.01)

(58) Field of Classification Search
CPC .......... F16H 1/32; F16H 57/082; B25B 17/02
See application file for complete search history.

(56) References Cited

U.S. PATENT DOCUMENTS 4,040,311 A * 8/1977 Page, Jr. .................. B23Q 5/14
                                                          433/105
4,347,762 A * 9/1982 Holdeman ................ F16H 3/54
                                                          475/298
(Continued)

FOREIGN PATENT DOCUMENTS

| EP | 0105430 A1 * | 4/1984 | ............... B25F 3/00 |
| WO | 9304304 | 3/1993 | |
| WO | WO-2013037325 A1 * | 3/2013 | ............. B25B 15/00 |

OTHER PUBLICATIONS

Failure Analysis Journal, pp. 1-20; published Aug. 1978. (Year: 2021).*

(Continued)

*Primary Examiner* — Tisha D Lewis
(74) *Attorney, Agent, or Firm* — Ferguson Case Orr Paterson

(57) ABSTRACT

A single use integrated disposable rotational speed reduction assembly having a shaft assembly, a housing, a planet carrier having a gear with inward-facing gear teeth, and one or more internal gear components with gear teeth. The shaft assembly causes rotation of the planet carrier with a sun gear via engagement with the internal gear components. The rotation of the internal gear components causes rotation of the planet carrier, with a reduction of rotational speed relative to the rotation of the shaft assembly. One or more gear components can be configured to fail after a predetermined number of use cycles.

14 Claims, 5 Drawing Sheets

(51) Int. Cl.
   *F16H 57/08* (2006.01)
   *B25B 17/02* (2006.01)

(56) References Cited

U.S. PATENT DOCUMENTS

| | | | |
|---|---|---|---|
| 4,791,833 | A | 12/1988 | Sakai |
| 5,269,733 | A | 12/1993 | Anthony, III |
| 5,993,454 | A | 11/1999 | Longo |
| 8,968,148 | B2 | 3/2015 | Matsuoka |
| 10,364,872 | B2 * | 7/2019 | Keeney .................. B60K 17/16 |
| 2013/0161040 | A1 | 6/2013 | Tomayko |
| 2015/0047463 | A1 | 2/2015 | Hofmann |

OTHER PUBLICATIONS

WO2013037325 machine translation, filed Jul. 29, 2021 (Year: 2021).*
Orientalmotor, (Oct. 12, 2017), URL: https://www.orientalmotor.com/ac-motors-gear-motors/torque-motors-tk.html, (Dec. 14, 2018), XP055613669.
EPO Communication pursuant to Rules 70(2) and 70a(2) EPC of Application No. 18873224.2 dated Dec. 12, 2021.
Extended European Search Report of Application No. 18873224.2 dated Nov. 15, 2021.

* cited by examiner

SECTION B-B

SECTION C-C

SECTION A-A

SINGLE USE GEAR REDUCTION DEVICE

CROSS-REFERENCE TO RELATED APPLICATIONS

This application claims the benefit of U.S. Provisional Patent Application No. 62/580,936 filed Nov. 2, 2017, the contents of which are incorporated in their entirety as if fully set forth herein.

TECHNICAL FIELD

This disclosure relates generally to single use rotational speed reduction devices and methods.

BACKGROUND

Tools used in different industries operate at many different speeds, and controlling the speed of operation is sometimes necessary. The need for carefully controlled speed of resecting tools often used in surgery is well known. Tools used during medical procedures must meet a predetermined level of sterilization. The financial and societal costs of infections caused by improperly sterilized items used during surgery are significant. Maintaining and sterilizing speed reduced powered tools used during medical procedures adds to the cost of health care.

DISCLOSURE

Many rotational tools (e.g. drills) operate at very high velocities, and it is sometimes necessary to reduce or limit how fast such tools spin. In the medical field, torque limiting devices in the operational theater are useful to reduce variables associated with fastening medical devices. However, unrestricted high-speed device operation may add unnecessary risk variables to a procedure.

According to aspects of some exemplary implementations of the disclosure, single use speed reduction systems are provided that comprise a shaft assembly comprising a drive shaft and a sun gear having a plurality of gear teeth, with the sun gear attached to or integral to the drive shaft, a housing, one or more internal gear components having a plurality of gear teeth, a planet carrier having a gear comprising inward-facing gear teeth, with one or more of gears being non-metal. In some implementations, the one or more internal gear components comprise a planet gear and a gear ring, the planet gear comprises a top portion and a bottom portion, with each portion having a plurality of gear teeth thereon, the gear ring comprises a plurality of outward-facing gear teeth, and the planet carrier comprises a plurality of inward-facing gear teeth around an edge of a recess in the top surface of the planet carrier, and the planet carrier is configured to rotate in response to rotation of the shaft assembly, via engagement between the sun gear and the top portion of the planet gear, engagement between the bottom portion of the planet gear and the gear ring, and engagement between the gear ring and the inward-facing teeth of the planet carrier. In some implementations, the one or more internal gear components comprise a gear ring, the gear ring comprises a top portion and a bottom portion, with the top portion having a plurality of inward-facing gear teeth thereon and the bottom portion having a plurality of outward-facing gear teeth thereon, and the planet carrier comprises a plurality of inward-facing gear teeth around an edge of a recess in the top surface of the planet carrier, and the planet carrier is configured to rotate in response to rotation of the shaft assembly, via engagement between the sun gear and the top portion of the gear ring and engagement between the bottom portion of gear ring and the inward-facing teeth of the planet carrier.

According to aspects of some exemplary implementations of the disclosure, single use speed reduction systems are provided that comprise a shaft assembly a comprising a drive shaft having a sun gear thereon, a housing, a planet gear having a top portion and a bottom portion, with each portion having a plurality of gear teeth thereon, a gear ring having a plurality of gear teeth, and a planet carrier having plurality of inward-facing gear teeth around the edge of the recess in the top surface of the planet carrier. In some implementations of the disclosure, the shaft is mated with the housing, and one or more of gears is non-metal.

According to aspects of some exemplary implementations of the disclosure, methods of reducing rotational velocity of a tool include a step of engaging a tool with an integrated speed reduction device as it is described in any of the embodiments throughout this application. The method also includes a step of operating the tool once it is engaged with the integrated speed reduction device.

DRAWINGS

The summary, as well as the following detailed description, is further understood when read in conjunction with the appended drawings. For the purpose of illustrating the disclosure, there are shown in the drawings exemplary implementations of the disclosure; however, the disclosure is not limited to the specific methods, compositions, and devices disclosed. In addition, the drawings are not necessarily drawn to scale.

Figure 1:
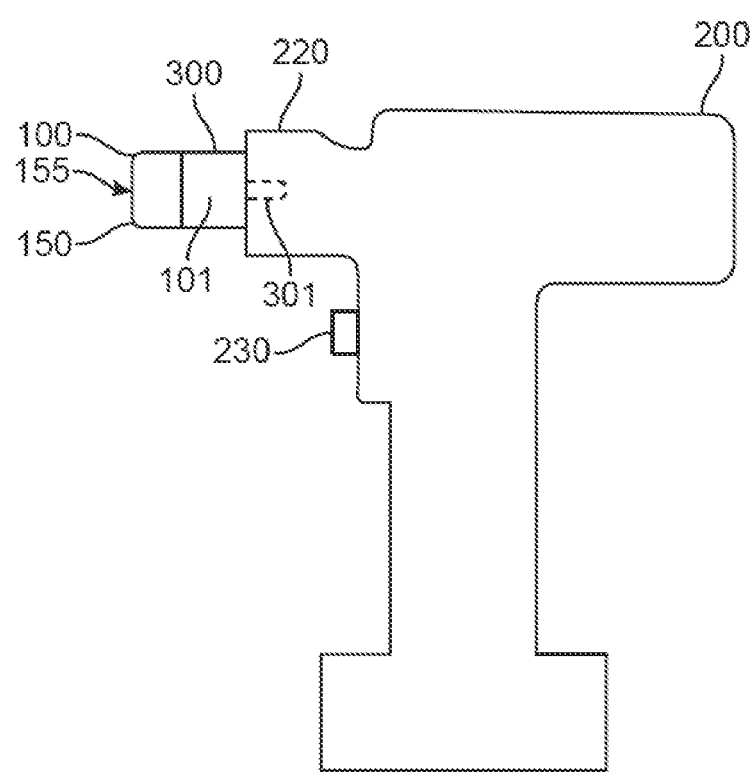
FIG. 1 is a schematic illustration of a side view of an embodiment of a rotational tool system including an implementation of an integrated rotational speed reduction assembly.

All reference numerals, designators, and call-outs in the figures are hereby incorporated by this reference as fully set forth herein. The failure to number an element in a figure is not intended to waive any rights, and unnumbered references may also be identified by alpha characters in the figures.

FURTHER DISCLOSURE

Some aspects of the disclosure will now be described in further detail with reference to the drawings, wherein like reference numbers refer to like elements throughout, unless specified otherwise. Certain terminology is used in the following description for convenience only and is not limiting.

For the purpose of illustrating the subject matter, there are shown in the drawings exemplary implementations of the subject matter; however, the presently disclosed subject matter is not limited to the specific methods, devices, and systems disclosed. In addition, the drawings are not necessarily drawn to scale.

The present disclosure may be understood more readily by reference to the following description taken in connection with the accompanying Figures and Examples, all of which form a part of this disclosure. It is to be understood that this invention is not limited to the specific products, methods, conditions or parameters described or shown herein, and that the terminology used herein is for the purpose of describing particular embodiments by way of example only and is not intended to be limiting of any claimed invention. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this text, it is recognized that the descriptions refer to apparatuses and methods of using said apparatuses. That is, where the disclosure describes or claims a feature or embodiment associated with an apparatus or a method of using an apparatus, it is appreciated that such a description or claim is intended to extend these features or embodiment to embodiments in each of these contexts apparatuses, methods of making, and methods of using).

In the present disclosure, the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the disclosure which are, for clarity, described herein in the context of separate exemplary implementations, may also be provided in combination in a single implementation. That is, unless obviously incompatible or specifically excluded, each individual exemplar is deemed to be combinable with any other exemplar(s) and such a combination is considered to be another exemplar. Conversely, various features of the disclosure that are, for brevity, described in the context of a single exemplar, may also be provided separately or in any sub-combination. Finally, while an exemplar may be described as part of a series of steps or part of a more general structure, each said step may also be considered an independent exemplar in itself, combinable with others.

The transitional terms "comprising," "consisting essentially of," and "consisting" are intended to connote their generally accepted meanings in the patent vernacular; that is, (i) "comprising," which is synonymous with "including," "containing," or "characterized by," is inclusive or open-ended and does not exclude additional, un-recited elements or method steps; (ii) "consisting of" excludes any element, step, or ingredient not specified in the claim; and (iii) "consisting essentially of" limits the scope of a claim to the specified materials or steps "and those that do not materially affect the basic and novel characteristic(s)."Exemplars described in terms of the phrase "comprising" (or its equivalents), also provide, as exemplars, those which are independently described in terms of "consisting of" and "consisting essentially" of.

When a list is presented, unless stated otherwise, it is to be understood that each individual element of that list, and every combination of that list, is a separate exemplar. For example, a list of exemplars presented as "A, B, or C" is to be interpreted as including the exemplars, "A," "B," "C," "A or B," "A or C," "B or C," "A, B, or C."

Throughout this specification, words are to be afforded their normal meaning, as would be understood by those skilled in the relevant art. However, so as to avoid misunderstanding, the meanings of certain terms will be specifically defined or clarified.

FIG. 1 depicts aspects of an implementation of a medical power tool system incorporating implementations of an integrated rotational speed reduction assembly 100. A medical power tool 200 with one or more actuation buttons 230 and an output mechanism 220 can be used. Output mechanism 220 can include a recessed opening that contains the output connection. Many standard types of output connections are known to those of skill in the art, including AO small, AO large, Trinkle, Hudson, Harris, and Zimmer. Integrated rotational speed reduction assembly 100 has a housing 101 with an interface system 300, which can be connected to output mechanism 220 and affixed in place such that the output connection is connected to a drill connection shaft 301 that is part of a shaft assembly 500 within the integrated rotational speed reduction assembly 100. Housing 101 can be provided with an interface system 300 having a retaining feature 310 that is used to lock the housing 101 in place relative to the output mechanism 220, such that the housing 101 does not rotate, but drill connection shaft 301 may rotate as it is driven by the medical power tool 200. A quick-turn retaining feature 310 is depicted in FIGS. 4-9, but alternative retaining features such as helical threading or fasteners could also be used. Retaining features of interface system 300 have been omitted from FIGS. 2-3 for illustrative purposes, but any suitable retaining feature described herein could be provided on housing 101. Drill connection shaft 301, also referred to herein as a drive shaft, can be configured with a variety of end profiles and connection types in order to interface with the output mechanism utilized in the particular power tool 200 being used in the system. Actuation button 230 can be utilized by a user to activate an internal motor of the power tool 200 (not shown) that transmits rotational force to output mechanism 220 and causes the mechanism to rotate.

Housing 101 is configured to interface with a planet carrier 150 to enclose internal components and form an integrated rotational speed reduction assembly 100. Housing 101 is mated to the planet carrier 150. The housing 101 and planet carrier 150 can be mated by the drill connection shaft 301, which has retaining features 505/506 which interface with portions of the housing 101 and the planet carrier 150 to hold them in close proximity, as described more fully elsewhere herein. At a distal end 155 of the planet carrier 150, a workpiece interface is included to provide for transfer of rotational torque to a workpiece (not shown). In FIGS. 2-6 the workpiece interface is illustrated conceptually as a stepped profile around the outer surface of the distal end 155, but in other implementations the workpiece interface can be a tip connection disposed within a central portion of the distal end 155 or any other element that is rigidly fixed to rotate with the planet carrier 150. The tip connection can be configured to interface with a workpiece or another workpiece-engaging component (not shown or further described herein). Tip connection can be implemented as one of many connection types, including a female AO type connection, AO small, AO large, Trinkle, Hudson, Harris, Zimmer, ¼-inch square, socket wrenches, or other profiles. In some implementations, tip connection can be configured with a workpiece-engaging profile for direct use on a workpiece or fastener. Some suitable configurations for tip connection and workpiece engaging tips are disclosed in U.S. Patent Publication No. US2013/0226192 A1, which is incorporated by reference herein in its entirety. In some implementations tip connection can also be configured to accept a keyed or keyless drill chuck with jaws that can clamp a variety of tools including drills and drivers.

In some implementations a shaft assembly 500 is configured to receive torque input to the integrated rotational speed reduction assembly 100 via the drill connection shaft 301. Some implementations of shaft assembly 500 are shown in FIGS. 2-5. The shaft assembly 500 can be formed as a singular piece, or in the alternative, it may be an assembly of multiple pieces. The shaft assembly 500 may be solid or hollow. The shaft assembly 500 may be solid throughout, hollow throughout, or solid in one or more locations and hollow in one or more locations. The shaft assembly 500 may include various materials, such as, but not limited to, metals, plastics, or a combination of metals and plastics. It may be made of metals, such as, but not limited to stainless steel, aluminum, or other metal alloys. In a non-limiting embodiment, the shaft may be made of SAE 316 grade stainless steel. The shaft assembly 500 may also be made of plastics, such as, but not limited to high-density polyethylene, low-density polyethylene, polyvinyl chloride, polypropylene, acrylonitrile butadiene styrene, polycarbonate, polyurethane, maleimide, bismaleimide, melamine formaldehyde, polyetheretherketone, polymethyl methacrylate, polytetrafluoroethylent, or a combination of one or more of plastics in this list. The shaft assembly 500 can provide for the mating between housing 101 and planet carrier 150 through the incorporation of retaining features 505/506. Retaining features 505/506 may be raised edges, slits that snap-fit with raised features on the housing 101 or the planet carrier 150, slits or holes that are configured to hold retaining rings or cotter pins, or other systems known in the art that can serve to prevent relative axial movement between the retaining features 505/506 and the corresponding component. In some embodiments a low friction spacer 112 (not shown in the Figures) is disposed between a raised lip retaining feature 506 and a surface around a top opening 105 of the housing 101. The retaining features serve to provide retention of the housing 101 and the planet carrier 150 within close proximity of each other, retaining the housing 101 and the planet carrier 150 between the two retaining features 505/506 while allowing for relative rotation between the housing 101 and the planet carrier 150. Shaft assembly 500 includes a sun gear 501 with a plurality of gear teeth 510. Shaft assembly 500 can also include a cylindrical portion 515 disposed between the sun gear 501 and the retaining feature 505 at the distal end opposite from the proximal end having the drill connection shaft 301.

Some implementations of shaft assembly 500 are formed from a drill connection shaft 301 that mates with a separate component sun gear 501. In some implementations, the sun gear 501 includes an opening 509 through a central axis (not shown), and the opening 509 can have a geometric profile that is complementary with a shaped portion 508 (not shown) of the drill connection shaft 301. The corresponding geometric profiles provide a rigid connection that allows for the transmission of torque.

In some implementations of the shaft assembly 500, the assembly is formed as one integral component that includes the sun gear 501 and the drive shaft 301. Shaft assembly 500 can be formed by machining or by molding.

In some implementations, relative movement between components can be unproved by making one or more components out of material that has a low coefficient of friction when in contact with another surface, coating the above components with a material that has a low coefficient of friction when in contact with another surface, applying a lubricant to the above components, positioning one or more low-friction spacers between adjacent components undergoing relative motion or rotation, or any combination of approaches in this list. One or more of the low-friction spacers may be constructed of a material or layers of material wherein after being exposed to a predetermined amount of friction and activity the material degrades or a layer is worn away exposing a layer which is easily degraded thereby adding debris to the internal volume of the integrated rotational speed reduction assembly 100 causing failure. In some implementations, a surface roughness can be provided on one or more portions of one or more surface components in order to impart a desired amount of degradation to a low friction spacer and introduce debris into the internal volume of the speed reduction assembly in order to induce failure after a predetermined amount of operation.

In some aspects, the integrated rotational speed reduction assembly 100 may be disposable. The integrated rotational speed reduction assembly 100 may be used for a predetermined number of uses. Alternatively, the integrated rotational speed reduction assembly 100 may be used for a predetermined duration of time. In some aspects, the integrated rotational speed reduction assembly 100 is intended for singular use. In further aspects, the reduction assembly is intended to be used for a predetermined number of rotations. In some aspects, the entire integrated rotational speed reduction assembly 100 is intended to be disposed of after a fixed usage period. In other aspects, portions of the integrated rotational speed reduction assembly 100 are intended to be disposed of while other portions are intended to be reused.

The drive shaft 301 may attach to a rotational tool that rotates the shaft during operation, such as a medical power fool 200. The integrated rotational speed reduction assembly 100 may accept various rotational inputs. In some aspects, it may accept inputs of up to about 2000 rpm in rotational speed. In other aspects, it may accept higher rotational speed inputs. In some aspects of the disclosure, it may accept inputs of at least about 150 rpm; in some aspects, it may accept inputs of at least about 450 rpm; in some aspects, it may accept inputs of at least about 1000 rpm; in some aspects, it may accept inputs of at least about 1250 rpm. In some aspects, it may accept inputs of up to about 1 N-m, up to about 2 N-m, up to about 3 N-m, up to about 4 N-m, up to about 5 N-m, up to about 6 N-m, up to about 7 N-m, up to about 8 N-m, up to about 9 N-m, or up to about 10 N-m.

The integrated rotational speed reduction assembly 100 can be used in methods of reducing rotational speed includes connecting a rotational tool to an integrated rotational speed reduction assembly, such as one described herein, and then operating the rotational tool. The method may further include a step of disconnecting the rotational tool from the reduction assembly. The method may further include a step of disposing of the tool, the reduction assembly, or both after an acceptable number of uses or after an acceptable duration of use. The method may further include a step of connecting the reduction assembly to a second tool. The connection of the second tool may be made before connection of the first tool, after connection of the first tool, or while the first tool is connected. In some aspects, more tools may be connected in a variety of acceptable orders. The method may further include a step of connecting a torque limiting device to the integrated rotational speed reduction assembly.

The integrated rotational speed reduction assemblies described herein can provide for predetermined rotational speed reduction ratios. The rotational speed reduction ratio is determined by the relative number of gear teeth provided on the sun gear 501, top and bottom portions of the planet gear 120, top and bottom portions of gear ring 700, and the gear ring formed of gear teeth 710/810 in the planet carrier 150, and the relative sizes of the gears. The gearing ratio represents the reduction in rotational speed, such that, for example, a value of 5:1 indicates that an input speed of 1000 rpm would create an output speed of 200 rpm. In some implementations, the gearing ratio can be provided as about 2.5:1, about 3:1, about 3.5:1, about 4:1, about 45:1, about 5:1, about 5.5:1, about 6:1, about 7:1, about 8:1, about 9:1, about 10:1, or about 11:1. Input torque is increased by the gearing ratio to produce a correspondingly higher output torque (before efficiency losses).

In some instances one or more of the drive shaft 301, the sun gear 501, gear ring 121, gear ring 700, and planet gear 120 are constructed of a material which is frangible or will otherwise fail after a predetermined number of cycles. A cycle for purposes of understanding the exemplar is the distance to complete one rotation of one of the drive shaft and planet carrier 150.

Preordained failure is used as an aspect of systems and methods disclosed herein to render the disposable device inoperable (within its use parameters) after a predetermined number of use cycles. In the medical arena, single use tools benefit from lower cost materials which are suitable for limited use cycles. Tool construction for a single use device also allows for designs which may have cavities and portions not amenable to subsequent re-sterilization, thus further providing opportunity for a reduction in health care costs. Risks associated with the improper reuse of single use or disposable tools include but are not limited to contamination, infection, failure during reuse, out of specification performance, damage to the mechanism during attempted re-sterilization. In some instances about 500 cycles at a predetermined force of Newton-meters is the preordained failure. In some instances between about 400 and about 600 cycles at a predetermined force of Newton-meters is the preordained failure. In some instances between about 200 and about 400 cycles at a predetermined force of Newton-meters is the preordained failure. In some instances between about 500 and about 1000 cycles at a predetermined force of Newton-meters is the preordained failure.

A. Planet Gear Systems

Figure 2:
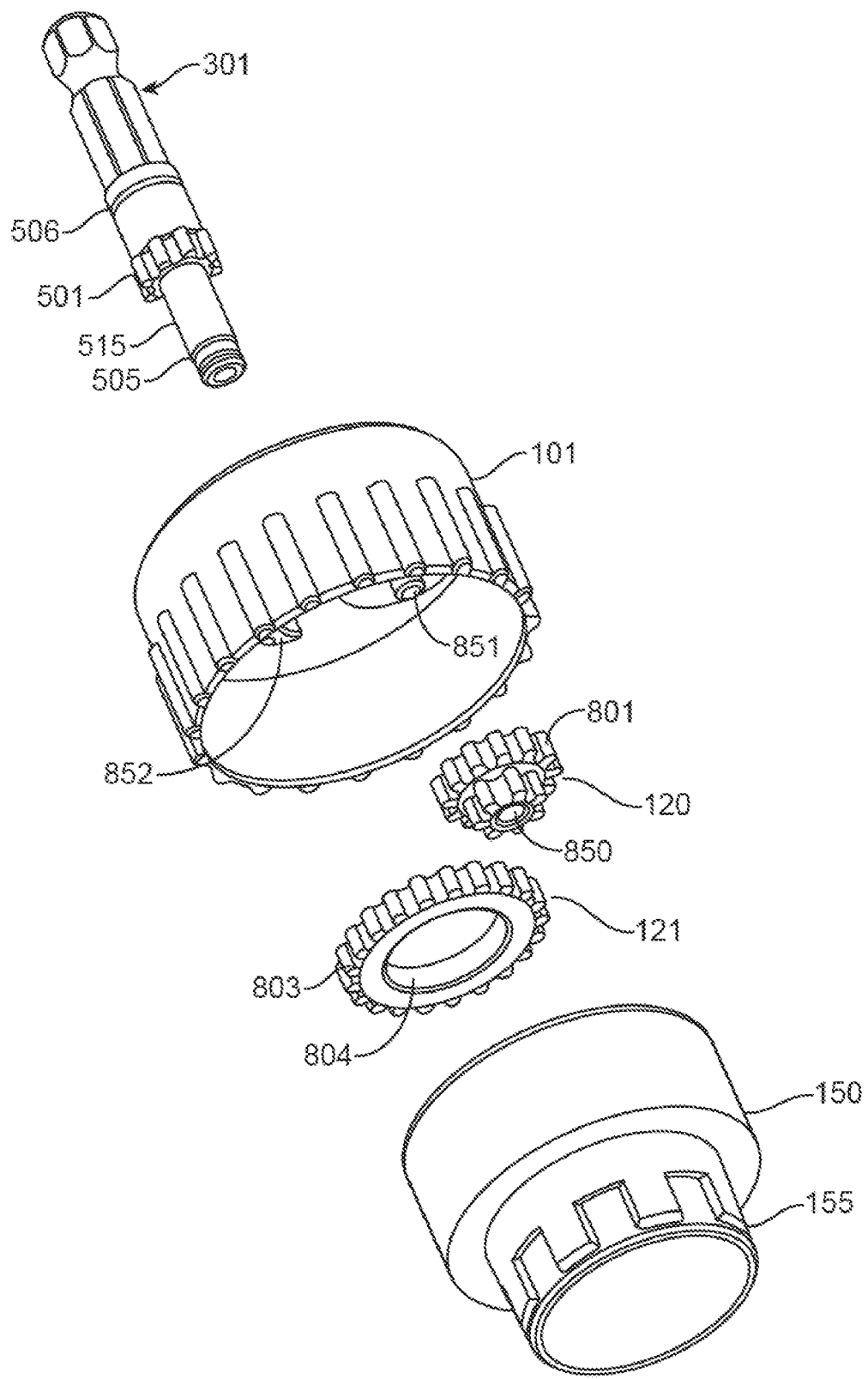
FIG. 2 is an exploded view of an embodiment of an integrated rotational speed reduction assembly.
Figure 3:
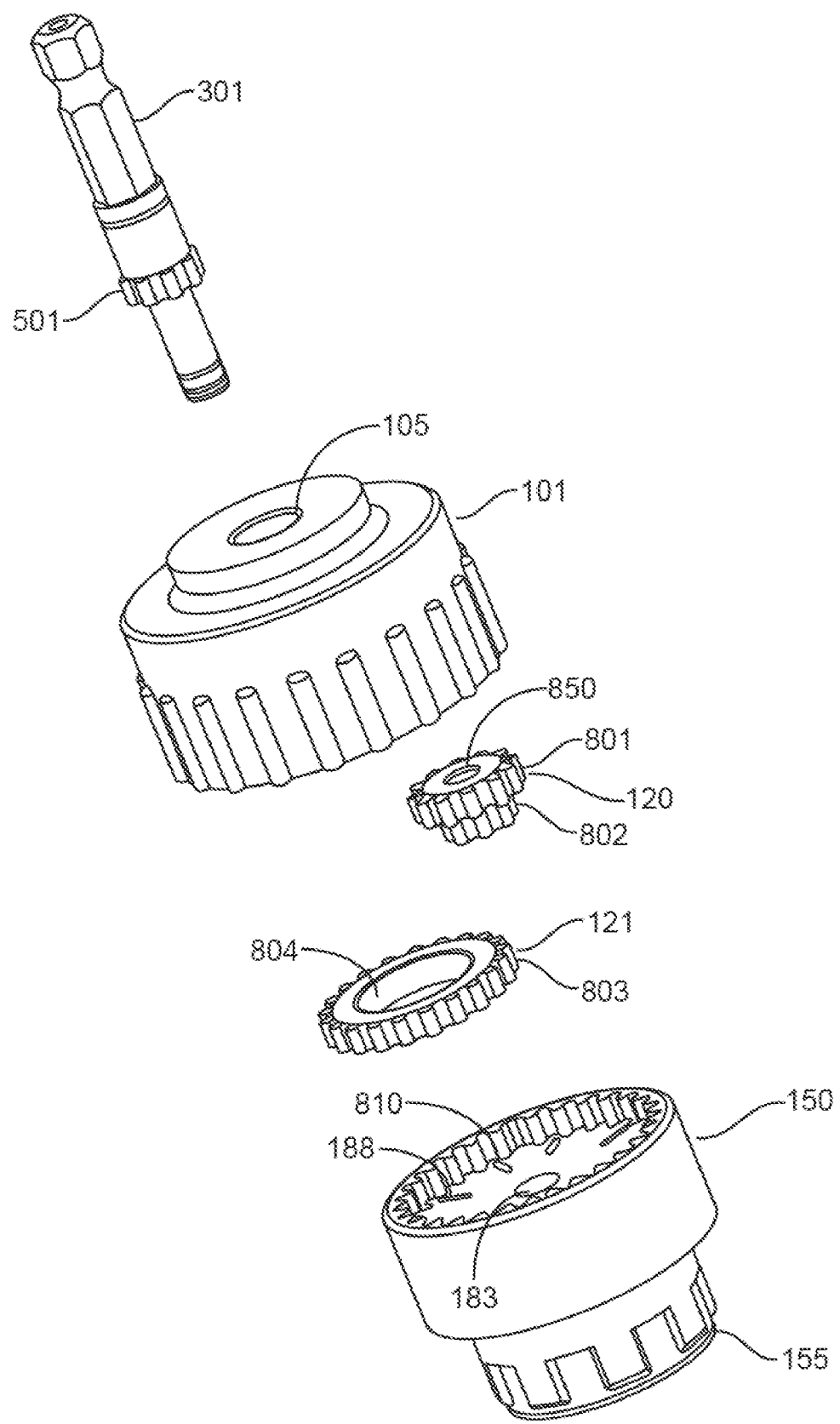
FIG. 3 is an exploded view from a different angle of the integrated rotational speed reduction assembly embodiment shown in FIG. 2.
Figure 5:
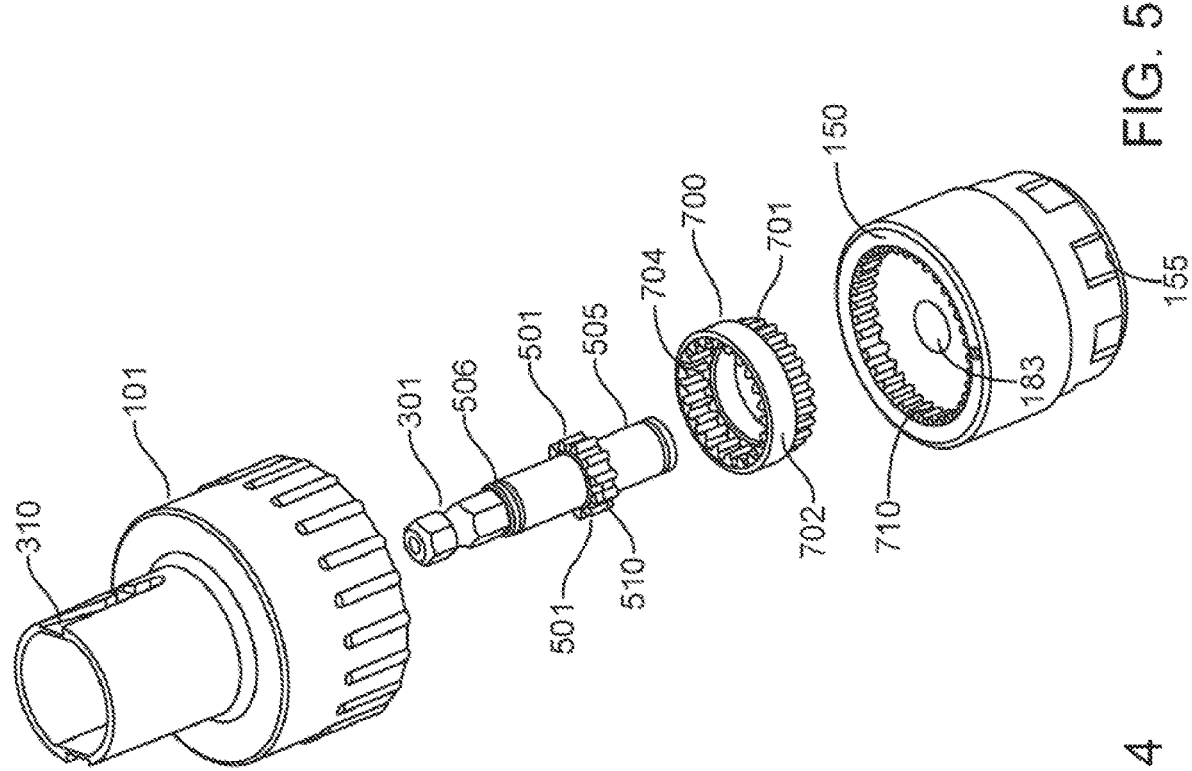
FIG. 5 is an exploded view from a different angle of the integrated rotational speed reduction assembly embodiment shown in FIG. 4.
Figure 4:
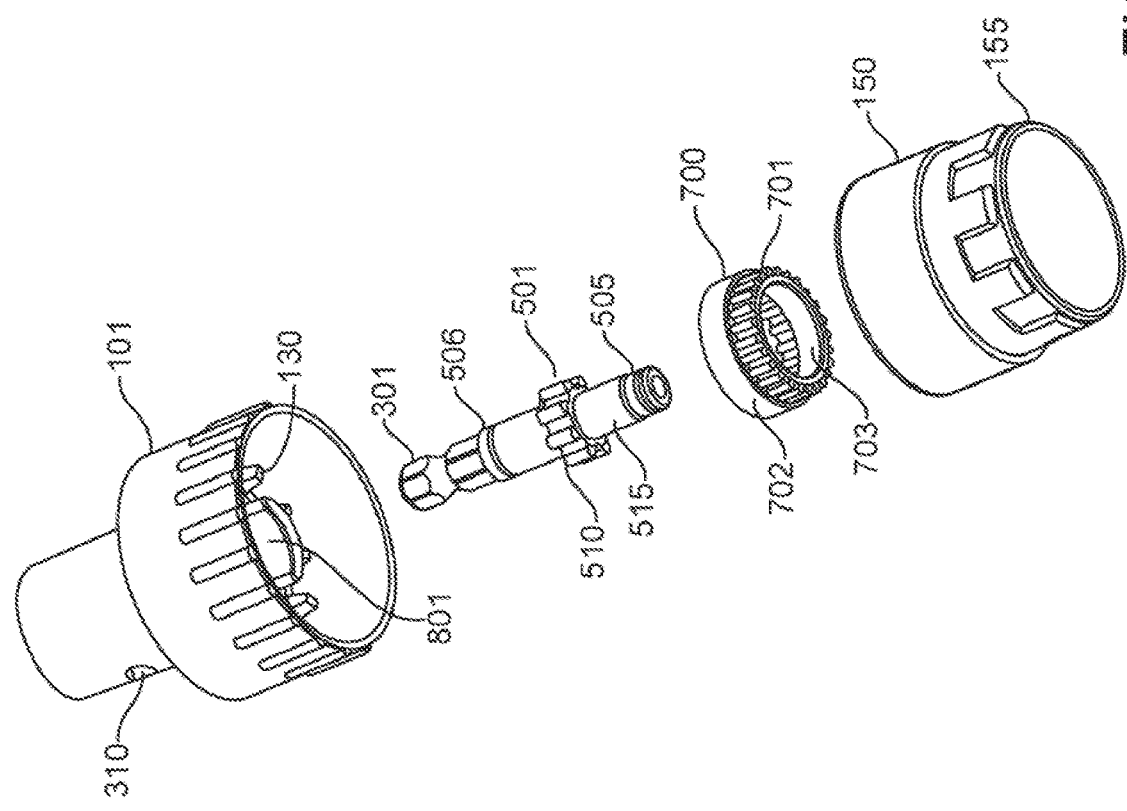
FIG. 4 is an exploded view of an embodiment of an integrated rotational speed reduction assembly.
Figure 6:
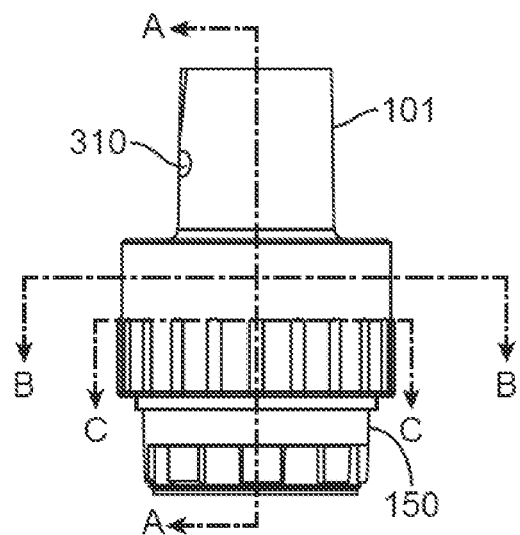
FIG. 6 is a side view of the integrated rotational speed reduction assembly shown in FIG. 5.

In some exemplary implementations, the planet carrier 150 is mechanically connected to the shaft assembly 500 by an internal gear train that comprises a planet gear 120 and a gear ring 121, as shown in non-limiting FIGS. 2 and 3. The sun gear 501 of the shaft assembly 500 is mated with the planet gear 120, with the plurality of sun gear teeth 510 mechanically meshing with a first set of gear teeth 801 disposed on a top portion of the planet gear 120. Planet gear 120 is formed with a central axis having a central axial bore 850, the first set of gear teeth 801 disposed on the top portion of the planet gear 120, and a second set of gear teeth 802 disposed on a bottom portion of the planet gear 120. The planet gear 120 is disposed on a planet gear pin 851 that is provided on an internal face of the housing 101, with the central axial bore 850 surrounding the planet gear pin 851 such that the planet gear 120 is stabilized axially but can rotate freely in place. Planet gear pin 851 can be formed as an integral feature of the housing 101 or can be formed separately and then attached to the housing 101 via a press-fit, adhesive, threaded connection, or other connection method known in the art, provided that the planet gear pin 851 is aligned perpendicular to the top inside surface of the housing 101 and has its central axis parallel to the central axis of the shaft assembly 500. A shallow recess can be provided in the top inside surface of the housing 101 to mate with a portion of the top portion of the planet gear 120 in order to enclose a portion of the plurality of gear teeth 801 and provide for further stabilization and retention of the planet gear 120.

In some exemplary implementations, the first set of gear teeth 801 and the second set of gear teeth 802 can have the same number of gear teeth or different numbers of gear teeth. In some implementations the second set of gear teeth 802 is formed with fewer gear teeth than the first set of gear teeth 801, and the bottom portion of the planet gear 120 has a smaller diameter than the top portion of the planet gear 120.

In some exemplary implementations, rotational torque input to the shaft assembly 500 is transferred through the internal gear train to the planet carrier 150. Rotation of the sun gear 501 causes corresponding rotation in the planet gear 120 through the mechanical mating of the gear teeth 510 and gear teeth 801. The rotation of the planet gear 120 causes rotation of the gear ring 121 through the mechanical mating of gear teeth 802 on the planet gear 120 and a plurality of gear teeth 803 of the gem ring 121. Gear ring 121 is formed as an annular ring having an smooth internal surface 804 and an outer surface having the plurality of gear teeth 803. Gear ring 121 is disposed within a recess in the top surface of the planet carrier 150, with the plurality of gear teeth 803 mechanically mating with a plurality of inward-facing gear teeth 810 around the edge of the recess in the top surface of the planet carrier 150. Gear ring 121 is thus disposed between the gear teeth 802 of the bottom portion of the planer gear 120 and the inward-facing gear teeth 810 of the planet carrier 150. Gear ring 121 is further retained by a crescent-shaped retainer 852 in the housing 101. Crescent-shaped retainer 852 provides a retaining surface that mates with the internal surface 804 of the gear ring 121 to maintain the mechanical mating between gear teeth 803 and gear teeth 810. If torque is applied to the shaft assembly 500 from a rotational tool and the housing 101 is fixed in place relative to the applied torque, shaft assembly 500 and sun gear 510 will rotate. This rotation of the sun gear 510 causes rotation of the planet gear 120 through mechanical mating between the gear teeth 510 and gear teeth 801. As planet gear 120 rotates, the set of gear teeth 802 rotate and mechanically mate with gear teeth 803 of the gear ring 121. Gear ring 121 is thus forced to rotate, causing gear teeth 803 to create rotation in the planet carrier 150 by the mechanical mate between gear teeth 803 and gear teeth 810. This rotation of planet carrier 150 causes rotation of the distal end 155 and any workpiece-engaging interface included therein.

Figure 7:
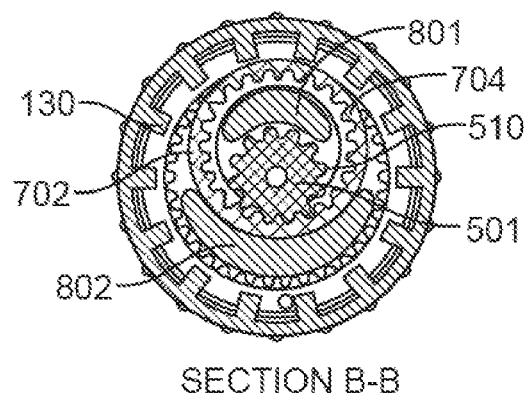
FIG. 7 is a cross-sectional view of the integrated rotational speed reduction assembly shown in FIGS. 5 and 6, along Section B-B depicted in FIG. 6.

In some exemplary implementations, the retainer 852 can have a cross-section similar to the crescent-shape cross-section of element 801 depicted in in FIG. 7. Such a shape can provide for a larger angle of contact along the internal surface 804 than a pin or rod would, and the crescent shape provides free space within the central opening of the gear ring 121 for the bottom portion of the shaft assembly 500, including cylindrical portion 515. Retainer 852 can contact the internal surface 804 along about 5 degrees, about 10 degrees, about 15 degrees, about 20 degrees, about 25 degrees, about 30 degrees, about 35 degrees, about 40 degrees, about 45 degrees, about 50 degrees, about 55 degrees, about 60 degrees, about 65 degrees, about 70 degrees, about 75 degrees, about 80 degrees, about 85 degrees, about 90 degrees; about 95 degrees; about 100 degrees; about 105 degrees; about 110 degrees; about 115 degrees; about 120 degrees; about 125 degrees; about 130 degrees; about 135 degrees, about 140 degrees, about 145 degrees, about 150 degrees, about 155 degrees, about 160 degrees, about 165 degrees, about 170 degrees, about 175 degrees, or about 180 degrees of the internal surface. In some preferred exemplary implementations, the retainer 852 can contact the internal surface 804 along between 150 degrees and about 180 degrees of the internal surface. The retainer 852 can be formed as an integral feature of the housing 101 or be formed separately and their attached to the housing 101 via a press-fit, adhesive, or other fastening method known in the art, provided the retainer extends perpendicularly from the inside surface of the housing 101 parallel to the central axis of the shaft assembly 500.

In some exemplary implementations, the planet carrier 150 can include a recess in the top surface of the planet carrier 150, with a plurality of inward-facing gear teeth 810 around the edge of the recess in the lop surface. The bottom surface of the recess can include one or more slots of holes 188 to retain lubricant or catch any debris generated during use. Planet carrier 150 is provided with a central axial bore 183 that contains a mating feature (not shown in FIGS. 2-3) that mates with mating feature 505 of the shaft assembly, as described more fully elsewhere herein. The mating connection between mating feature 505 and the corresponding feature in the central axial bore 183 serves to retain the planet carrier 150 to the housing 101 while providing for free relative rotation between the two components.

B. Compound Gear Ring Systems

In some exemplary implementations, the planet carrier 150 is mechanically connected to the shaft assembly 500 by an internal gear train that comprises a compound gear ring 700, as shown in non-limiting FIGS. 4-9, The compound gear ring 700 is formed as an annular ring having a top portion and a bottom portion. The bottom portion is formed with a smooth internal surface 703 and an outer surface having the plurality of gear teeth 701. The top portion is formed with smooth external surface 702 and a plurality of inward-facing gear teeth 704. Gear ring 700 is disposed with the bottom portion resting within a recess in the top surface of the planet carrier 150, with the plurality of gear teeth 701 mechanically mating with a plurality of inward-facing gear teeth 710 around the edge of the recess in the top surface of the planet carrier 150. Gear ring 700 is disposed with the top portion resting between features of the housing 101. Gear ring 700 is disposed such that the smooth external surface 702 is retained by one or more of a plurality of retention bumps 130 and a crescent-shaped retaining feature 802. Retaining feature 802 makes contact with the smooth external surface 702 at one portion of its length (along the inner edge/side) and makes contact with the plurality of gear teeth 710 of the planet carrier 150 at another portion of its length (the outer edge/side). The retaining feature 802 allows for relative rotation of the gear ring 700 and planet carrier 150 while providing for aligning contact with those components. Gear ring 700 is further retained by a crescent-shaped retaining feature 801 of the housing 101. Retaining feature 801 provides aligning contact with a portion of the smooth internal surface 703 of the bottom portion of the gear ring 700. As explained more fully elsewhere herein, housing 101 is mated with planet carrier 150 via the retaining features 505/506 of the drive shaft 301, which interface with portions of the housing 101 and the planet carrier 150 to hold them in close proximity.

Figure 8:
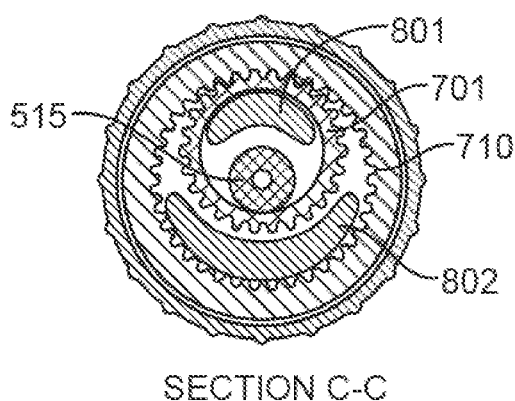
FIG. 8 is a cross-sectional view of the integrated rotational speed reduction assembly shown in FIGS. 5-7, along Section C-C depicted in FIG. 6.
Figure 9:
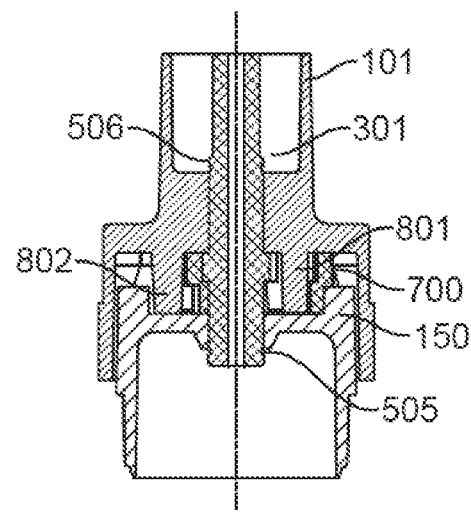
FIG. 9 is a cross-sectional view of the integrated rotational speed reduction assembly shown in FIGS. 5-8, along Section A-A depicted in FIG. 6.

In some exemplary implementations, the retainer 801 can have a crescent-shape cross-section as depicted in FIGS. 7-8. Such a shape can provide for a larger angle of contact along the internal surface 703 than a pin or rod would, and the crescent shape provides free space within the central opening of the gear ring 700 for the bottom portion of the shaft assembly 500, including cylindrical portion 515. Retainer 801 can contact the internal surface 703 along about 5 degrees, about 10 degrees, about 15 degrees, about 20 degrees, about 25 degrees, about 30 degrees, about 35 degrees, about 40 degrees, about 45 degrees, about 50 degrees, about 55 degrees, about 60 degrees, about 65 degrees, about 70 degrees, about 75 degrees, about 80 degrees, about 85 degrees, about 90 degrees, about 95 degrees, about 100 degrees, about 105 degrees, about 110 degrees, about 115 degrees, about 120 degrees, about 125 degrees, about 130 degrees, about 135 degrees, about 140 degrees, about 145 degrees, about 150 degrees, about 155 degrees, about 160 degrees, about 165 degrees, about 170 degrees, about 175 degrees, or about 180 degrees of the internal surface. In some preferred exemplary implementations, the retainer 801 can contact the internal surface 703 along between 150 degrees and about 180 degrees of the internal surface. The retainer 801 can be formed as an integral feature of the housing 101 or be formed separately and then attached to the housing 101 via a press-fit, adhesive other fastening method known in the art, provided the retainer extends perpendicularly from the inside surface of the housing 101 parallel to the central axis of the shaft assembly 500.

In some exemplary implementations, the retainer 802 can have a crescent-shape cross-section as depicted in FIGS. 7-8. Such a shape can provide for a larger angle of contact along the external surface 702 than a pin or rod feature would, and the outer edge of the carrier-shape cross-section makes contact with the plurality of gear teeth 710 of the planet carrier 150 to further aid in maintaining alignment between the housing 101 and the planet carrier 150. The retainer 802 can contact the external surface 702 along about 5 degrees, about 10 degrees, about 15 degrees, about 20 degrees, about 25 degrees, about 30 degrees, about 35 degrees, about 40 degrees, about 45 degrees, about 50 degrees, about 55 degrees, about 60 degrees, about 65 degrees, about 70 degrees, about 75 degrees, about 80 degrees, about 85 degrees, about 90 degrees, about 95 degrees, about 100 degrees, about 105 degrees, about 110 degrees, about 115 degrees, about 120 degrees, about 125 degrees, about 130 degrees, about 135 degrees, about 140 degrees, about 145 degrees, about 150 degrees, about 155 degrees, about 160 degrees, about 165 degrees, about 170 degrees, about 175 degrees, or about 180 degrees of the internal surface. In some preferred exemplary implementations, the retainer 802 can contact the external surface 702 along between 150 degrees and about 180 degrees of the internal surface. The retainer 802 can contact the plurality of gear teeth 710 of the planet carrier 150 along about 5 degrees, about 10 degrees, about 15 degrees, about 20 degrees, about 25 degrees, about 30 degrees, about 35 degrees, about 40 degrees, about 45 degrees, about 50 degrees, about 55 degrees, about 60 degrees, about 65 degrees, about 70 degrees, about 75 degrees, about 80 degrees, about 85 degrees, about 90 degrees, about 95 degrees, about 100 degrees, about 105 degrees, about 110 degrees, about 115 degrees, about 120 degrees, about 125 degrees, about 130 degrees, about 135 degrees, about 140 degrees, about 145 degrees, about 150 degrees, about 155 degrees, about 160 degrees, about 165 degrees, about 170 degrees, about 175 degrees, or about 180 degrees of the internal surface. In some preferred exemplary implementations, the retainer 802 can contact the plurality of gear teeth 710 of the planet carrier 150 along between 150 degrees and about 180 degrees of the internal surface. The retainer 802 can be formed as an integral feature of the housing 101 or be formed separately and then attached to the housing 101 via a press-fit, adhesive, or other fastening method known in the art, provided the retainer extends perpendicularly from the inside surface of the housing 101 parallel to the central axis of the shaft assembly 500.

While the method and apparatus have been described in terms of what are presently considered to be the most practical and preferred implementations, it is to be understood that the disclosure need not be limited to the disclosed implementations. It is intended to cover various modifications and similar arrangements included within the spirit and scope of the claims, the scope of which should be accorded the broadest interpretation so as to encompass all such modifications and similar structures. The present disclosure includes any and all implementations of the following claims.

It should also be understood that a variety of changes may be made without departing from the essence of the disclosure. Such changes are also implicitly included in the description. They still fall within the scope of this disclosure. It should be understood that this disclosure is intended to yield a patent covering numerous aspects of the disclosure both independently and as an overall system and in both method and apparatus modes.

Further, each of the various elements of the disclosure and claims may also be achieved in a variety of manners. This disclosure should be understood to encompass each such variation, be it a variation of an implementation of any apparatus implementation, a method or process implementation, or even merely a variation of any element of these.

Particularly, it should be understood that as the disclosure relates to elements of the disclosure, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this disclosure is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary latest edition are hereby incorporated by reference.

In this regard it should be understood that for practical reasons and so as to avoid adding potentially hundreds of claims, the applicant has presented claims with initial dependencies only.

Support should be understood to exist to the degree requited under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular implementation, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative implementations.

Such terms should be interpreted in their most expansive forms so as to afford the applicant the broadest coverage legally permissible.

What is claimed:

1. A single use integrated rotational speed reduction assembly comprising:
    a shaft assembly comprising a drive shaft and a sun gear comprising a plurality of gear teeth, the sun gear attached to or integral to the drive shaft;
    a housing;
    one or more internal gear components, each comprising a plurality of gear teeth;
    a planet carrier comprising a gear comprising inward-facing gear teeth; and,
    wherein one or more gears is non-metal, wherein the shaft assembly provides for the mating between the housing and the planet carrier via one or more retaining features provided on the shaft assembly, wherein:
    the one or more internal gear components comprise a planet gear and a gear ring;
    the planet gear comprises a top portion and a bottom portion, with each portion comprising a plurality of gear teeth thereon;
    the gear ring comprises a plurality of outward-facing gear teeth; and
    the planet carrier comprises a plurality of inward-facing gear teeth around an edge of a recess in a top surface of the planet carrier;

the planet carrier is configured to rotate in response to rotation of the shaft assembly, via engagement between the sun gear and the top portion of the planet gear, engagement between the bottom portion of the planet gear and the gear ring, and engagement between the gear ring and the inward-facing teeth of the planet carrier.

2. The single use integrated rotational speed reduction assembly of claim 1, wherein the one or more non-metal teeth are frangible after a predetermined number of use cycles.

3. The single use integrated rotational speed reduction assembly of claim 2, wherein at least one of the frangible teeth will fail after a predetermined number of use cycles.

4. A single use integrated rotational speed reduction assembly comprising:
  a shaft assembly comprising a drive shaft and a sun gear comprising a plurality of gear teeth, the sun gear attached to or integral to the drive shaft;
  a housing;
  one or more internal gear components, each comprising a plurality of gear teeth;
  a planet carrier comprising a gear comprising inward-facing gear teeth; and,
  wherein one or more gears is non-metal, wherein the shaft assembly provides for the mating between the housing and the planet carrier via one or more retaining features provided on the shaft assembly, wherein:
  the one or more internal gear components comprise a gear ring;
  the gear ring comprises a top portion and a bottom portion, with the top portion comprising a plurality of inward-facing gear teeth thereon, and the bottom portion comprising a plurality of outward-facing gear teeth thereon; and
  the planet carrier comprises a plurality of inward-facing gear teeth around an edge of a recess in a top surface of the planet carrier;
  the planet carrier is configured to rotate in response to rotation of the shaft assembly, via engagement between the sun gear and the top portion of the gear ring and engagement between the bottom portion of gear ring and the inward-facing teeth of the planet carrier.

5. A single use speed reduction system comprising:
  a shaft assembly comprising a drive shaft comprising a sun gear thereon;
  a housing;
  a planet gear comprising a top portion and a bottom portion, with each portion comprising a plurality of gear teeth thereon;
  a gear ring comprising a plurality of gear teeth; and
  a planet carrier comprising plurality of inward-facing gear teeth around an edge of a recess in a top surface of the planet carrier;
  wherein the shaft is mated with the housing; and,
  wherein one or more gears is non-metal.

6. The single use speed reduction system of claim 5 wherein:
  the gear teeth of the top portion of the planet gear engage with the gear teeth of the sun gear;
  the gear teeth of the bottom portion of the planet gear engage with the gear teeth of the gear ring; and
  the gear teeth of the gear ring engage with the gear teeth of the bottom portion of the planet gear and with the inward-facing gear teeth of the planet carrier.

7. The single use speed reduction system of claim 6 wherein one or more non-metal teeth are frangible after a predetermined number of use cycles.

8. The single use speed reduction system of claim 7 wherein in at least one of the frangible teeth will fail after a predetermined number of use cycles.

9. A method for reducing rotational speed of one or more disposable rotational tools, the method comprising:
  connecting an input of the single use speed reduction system of claim 5 to a first rotational tool;
  operating the first rotational tool; and,
  whereby the single use speed reduction system reduces the rotational speed provided to the input and provides the reduced speed as an output.

10. The method of claim 9, wherein the ratio of speed input to output is between about 3:1 and about 5:1.

11. The method of claim 9, wherein the speed reduction assembly increases the torque applied to the input to a higher torque output.

12. A single use speed reduction system comprising:
  a shaft assembly comprising a drive shaft comprising a sun gear thereon;
  a housing;
  a gear ring comprising a top portion and a bottom portion, with the top portion comprising a plurality of inward-facing gear teeth thereon, and the bottom portion comprising a plurality of outward-facing gear teeth thereon; and
  a planet carrier comprising a plurality of inward-facing gear teeth around an edge of a recess in a top surface of the planet carrier;
  wherein the shaft is mated with the housing; and,
  wherein one or more of the gears is non-metal.

13. The single use speed reduction system of claim 12 wherein:
  the gear teeth of the top portion of the gear ring engage with the gear teeth of the sun gear; and
  the gear teeth of the bottom portion of the gear ring engage with the gear teeth of the inward-facing gear teeth of the planet carrier.

14. The single use speed reduction system of claim 13, wherein one or more non-metal teeth are frangible and will fail after a predetermined number of use cycles.

* * * * *